United States Patent [19]
Khosah et al.

[11] Patent Number: 4,816,159
[45] Date of Patent: Mar. 28, 1989

[54] SUPERCRITICAL FLUID CHROMATOGRAPHY PACKING MATERIAL

[75] Inventors: Robinson P. Khosah, Point Breeze; John W. Novak, New Kensington; Douglas G. Weaver, Monroeville; Karen R. Fraser-Milla, Wilkinsburg; Richard R. Burr, Leechburg, all of Pa.

[73] Assignee: Aluminum Company of America, Pittsburgh, Pa.

[21] Appl. No.: 90,880

[22] Filed: Aug. 31, 1987

[51] Int. Cl.⁴ ............................................. B01D 15/08
[52] U.S. Cl. ................................. 210/635; 210/659; 210/198.2; 210/502.1; 260/405.5; 260/410.7; 260/420; 260/428.5
[58] Field of Search ............ 210/635, 656, 659, 198.2, 210/502.1; 260/405.5, 410.7, 420, 428.5

[56] References Cited

U.S. PATENT DOCUMENTS

| | | | |
|---|---|---|---|
| 3,013,904 | 12/1961 | Cupery | 117/76 |
| 3,232,887 | 2/1966 | Pessimisis | 252/435 |
| 3,917,808 | 11/1975 | Leach et al. | 423/626 |
| 4,087,383 | 5/1978 | Gernand et al. | 252/463 |
| 4,123,931 | 11/1978 | Blaser | 73/23.1 |
| 4,183,843 | 1/1980 | Koenig et al. | 260/40 |
| 4,202,798 | 5/1980 | Johnson et al. | 252/437 |
| 4,251,350 | 2/1981 | Johnson et al. | 208/216 |
| 4,308,079 | 12/1981 | Venables et al. | 148/6.15 |
| 4,382,016 | 5/1983 | Rickelton et al. | 252/428 |
| 4,466,923 | 8/1984 | Friedrich | 260/410.7 |
| 4,478,720 | 10/1984 | Perrut | 210/659 |
| 4,479,380 | 10/1984 | Novotny et al. | 73/61.1 |
| 4,500,432 | 2/1985 | Poole | 210/659 |
| 4,506,628 | 3/1985 | Stockel | 119/1 |
| 4,648,975 | 3/1987 | Barkatt | 210/656 |
| 4,692,280 | 9/1987 | Spinelli | 260/420 |

*Primary Examiner*—Ernest G. Therkorn
*Attorney, Agent, or Firm*—Andrew Alexander

[57] ABSTRACT

Disclosed is a method of separating organic or organometallic materials under supercritical fluid conditions, the method comprising the steps of providing a bed of packing material selected from a metal oxide/hydroxide support material having phosphorous-containing organic molecules bonded to reactive sites on said support material, alumina and alumina-containing mixtures. The materials are introduced to the bed and a fluid is added to the bed under supercritical fluid conditions. The fluid removes one of the materials from the bed.

21 Claims, 5 Drawing Sheets

WEIGHT PERCENT OF PHOSPHORUS ADSORBED ONTO BAYERITE AND GAMMA ALUMINA AS A FUNCTION OF PHENYLPHOSPHONIC ACID CONCENTRATION

WEIGHT PERCENT OF PHOSPHORUS ADSORBED ONTO BAYERITE AND GAMMA ALUMINA AS A FUNCTION OF AGING TIME

CONCENTRATION OF PHOSPHORUS
REMAINING IN SOLUTION AFTER FILTRATION
AS A FUNCTION OF AGING TIME

COMPARISON OF THE WEIGHT PERCENT OF PHOSPHORUS
ADSORBED ONTO WASHED AND AS PREPARED GAMMA ALUMINA
AS A FUNCTION OF PHENYLPHONIC ACID CONCENTRATION

COMPARISON OF THE WEIGHT PERCENT OF PHOSPHORUS ADSORBED ONTO WASHED AND AS PREPARED GAMMA ALUMINA AS A FUNCTION OF AGING TIME pH OF THE 24 HOUR BAYERITE AND GAMMA ALUMINA TIME STUDY AS A FUNCTION OF AGING TIME

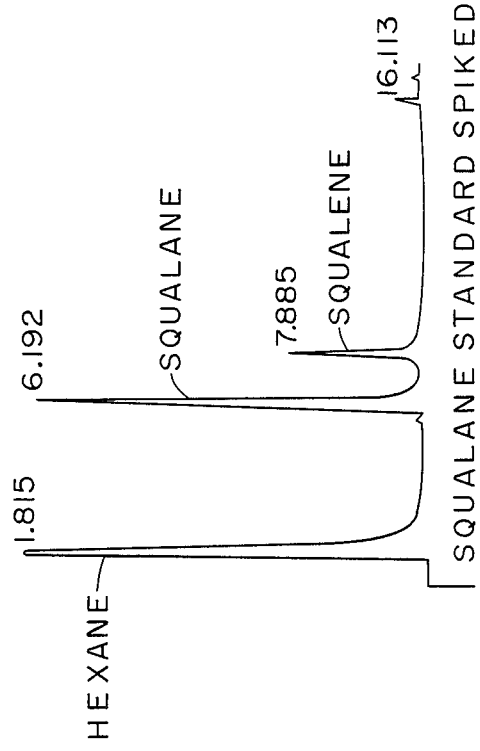
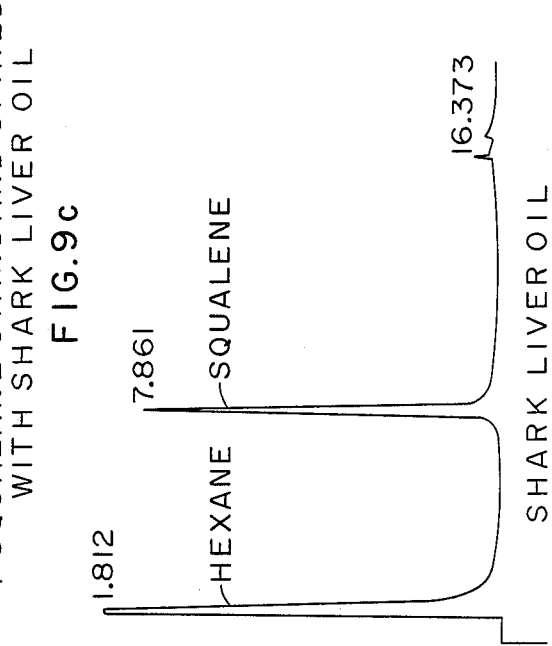
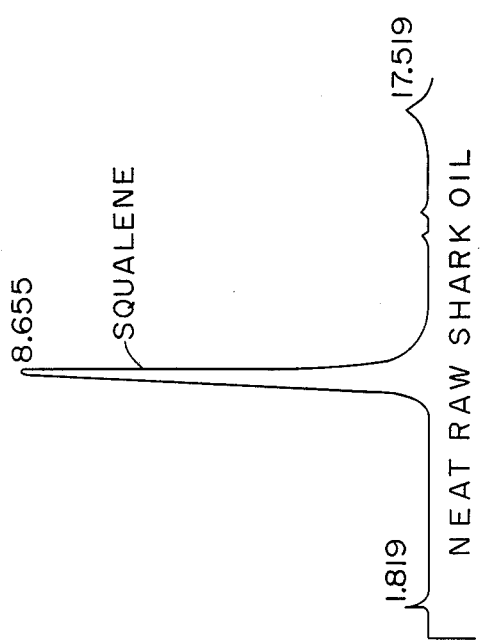
SEPARATION OF SHARK LIVER OILS BY SCF USING ALUMINA MICROPACKED COLUMNS

SUPERCRITICAL FLUID CHROMATOGRAPHY PACKING MATERIAL

BACKGROUND OF THE INVENTION

1. Field of the Invention

This invention relates to supercritical fluid chromatography or separations and column packing material therefor. More particularly, this invention relates to alumina packing material or a packing material comprising a metal oxide/hydroxide reacted with a phosphorous-containing acid, e.g., phosphonic or phosphinic acid, or phosphoric ester to form preferably a monomolecular layer thereon thereby providing a supercritical fluid chromatographic packing material having good pH stability as well as high efficiency.

2. Description of the Related Art

Chromatographic packing materials made from organic resins suffer from poor physical strength, poor thermal stability, high cost, solvent swelling, and low capacity. Chromatographic packing materials made from metal oxides such as silica exhibit poor chemical stability at high pH. For many applications, a chromatographic packing material which high physical integrity, good chemical stability over high and low pH conditions, specific surface functionalities, good thermal stability, and low cost is needed.

Other metal oxides such as alumina have been used as adsorbents because of the good physical integrity and low cost of alumina. The solubility of alumina in pH ranges between 4 and 9 is very low and the material is, therefore, chemically and physically stable in this pH range. However, beyond this pH range, on either the basic or acidic side, alumina becomes soluble in aqueous media and its physical strength and integrity degrades rapidly.

Modifications of metal oxide adsorbents such as alumina and aluminosilicates have been proposed. Stockel U.S. Pat. No. 4,506,628 teaches the formation of an adsorbent animal litter utilizing alumina, aluminosilicates, or coal residues as the substrate intimately mixed with monomers containing acid functionalities which polymerize in situ. The monomer, such as vinyl phosphonic acid, together with a redox catalyst, is mixed with a pliable dough formed from alumina and water and extruded into pellets which harden as the monomer polymerizes.

Modified alumina has also been used in the formation of catalysts. Johnson et al U.S. Pat. Nos. 4,202,798 and 4,251,350 describe the formation of a hydrocarbon hydrotreating catalyst formed by contacting alumina with a phosphorous-containing acid compound such as phenylphosphonic acid and then calcining the phosphorous-containing hydrous alumina. The calcined alumina is then treated with at least one metal-containing compound and again calcined to form the catalyst product.

In addition, Cupery U.S. Pat. No. 3,013,904 discloses a substrate having an organic polymer containing pentavalent phosphorus bonded thereto. Coatings of phosphorous-containing organic polymers are applied over coatings of positively charged colloidal metal oxides applied to negatively charged substrates. The thickness of the combined colloidal oxide and polymer layers on a substrate is less than 100 millimicrons.

Novotny et al U.S. Pat. No. 4,479,380 discloses an apparatus open-tube supercritical fluid chromatography wherein the apparatus has an elongated passageway having inlet and outlet ends such as a capillary column, coated or not with a coating having affinity for solute molecules to be analyzed. Coating materials include methyl and phenyl silicine polymers and adsorbents such as silica, alumina and activated carbon.

Venables et al U.S. Pat. No. 4,308,079 teaches the treatment of an aluminum oxide surface of an aluminum substrate with a monomolecular layer of an amino phosphonate compound such as nitrilotris (methylene) triphosphonic acid to retard hydration of the aluminum oxide to aluminum hydroxide to provide a more stable microporous surface which is particularly suited to commercial adhesives. The presence of the hydrated oxide is said to interfere with the formation of a satisfactory bond between the adhesive and the oxide, while the phosphonate treatment is said to inhibit the conversion of the oxide to hydroxide without interfering with subsequent bonding of the adhesive to the oxide.

SUMMARY OF THE INVENTION

A method of separating organic materials under supercritical fluid conditions is disclosed. The method comprises the steps of providing a bed containing alumina and introducing materials such as organic or organometallic materials to be separated to the bed of alumina. Supercritical fluid is added to the bed and then removed therefrom carrying with it at least one of the materials to be separated. The supercritical fluid and material removed from the bed are then separated.

Supercritical fluid chromatographic packing may be a metal oxide/hydroxide, e.g., alumina, derivatized material and columns or beds of such material may be used. The metal oxide/hydroxides have bonded to reactive sites on the surface thereof a monomolecular layer of one or more phosphorous-containing organic molecules, e.g., phosphonic or phosphinic acids or esters. The non-polar portion of the molecule is oriented away from the surface of the metal oxide/hydroxide particle for interaction with the materials being passed through the supercritical fluid chromatography column. That is, the organic molecule is comprised of a phosphorous-containing group capable of forming a chemical bond with reactive sites on the metal oxide/hydroxide particle and a carbon-containing group or site oriented away from the surface of the metal oxide/hydroxide particle and capable of functioning as the active component or site on the molecules.

It is, therefore, an object of this invention to provide a supercritical fluid chromatographic packing material.

It is another object of this invention to provide a supercritical fluid chromatographic packing material comprising a monomolecular layer of one or more phosphorous-containing acids bonded to the surface of a metal oxide/hydroxide particle.

It is yet another object of this invention to provide a supercritical fluid chromatographic packing material comprising a monomolecular layer of one or more phosphonic acids bonded to the surface of a metal oxide/hydroxide particle which is stable at extended pH ranges yet capable of high efficiency in separation of materials.

It is still another object of this invention to provide a bed of supercritical packing material comprised of alumina.

It is yet another object of this invention to provide a process for supercritical fluid extraction and purification of fatty acids and oils such as shark liver oil, olive oil and the like.

And yet it is another object of this invention to provide a process for supercritical fluid extraction and purification without the use of organic solvents.

These and other objects of this invention will be obvious from the following description and accompanying drawings.

BRIEF DESCRIPTION OF THE DRAWINGS

FIGS. 9a–9d are plots of chromatographic tests run on columns containing the packing material of the invention.

DETAILED DESCRIPTION OF THE INVENTION

Figure 1:
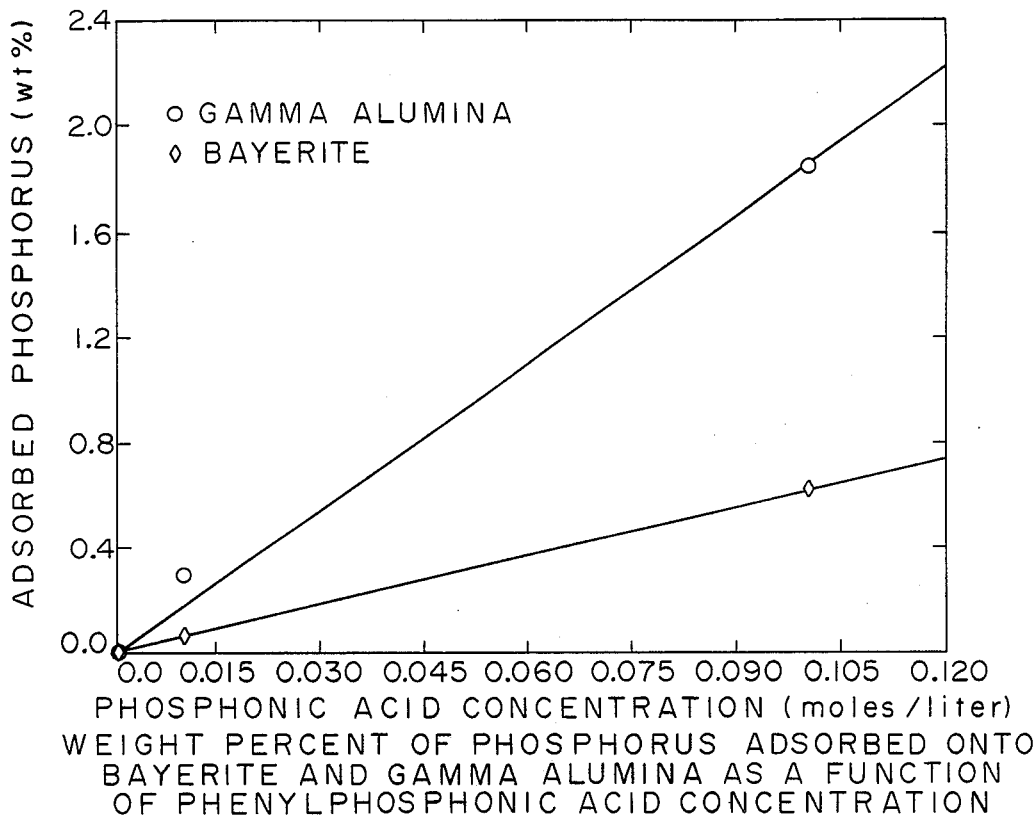
FIG. 1 is a graph showing the weight percent of phosphorus adsorbed to forms of aluminum oxide/hydroxide as a function of acid concentration.

In accordance with the invention, supercritical fluid packing material comprises alumina or a metal compound such as a metal oxide/hydroxide particle having chemically bonded thereto a substantially monomolecular layer of one or more phosphonic or phosphinic acids or esters.

The packing material may also be alumina combined or mixed with one or more other materials such as silica, carbon, diatomaceous earth, magnesium silicate and hydrotalcite. The combinations may contain from 5 to 95 wt. % alumina, preferably 30 to 70 wt. % alumina.

By the use of the term "metal compound" herein is meant a compound or mixture thereof to which can be bonded one or more phosphonic or phosphinic acids or esters, preferably substantially a monomolecular layer of such acids or esters.

The use of the term "metal oxide/hydroxides" herein is intended to define a broad spectrum of oxides ranging from those which may contain few hydroxides, e.g., activated forms of aluminum oxide (alumina) to more hydrated forms which may comprise mainly hydroxide, e.g., $Al(OH)_3$. It has been found, however, that the metal hydroxide form, rather than the metal oxide form, provides a better bond with the phosphorous-containing group on the organic molecule with which it is reacted. However, for certain applications, dehydrated or activated forms of the metal oxide/hydroxide may be preferred due to the higher surface area of such particles. For example, when an aluminum oxide/hydroxide is used, the hydrated form will be preferred, e.g., gibbsite, bayerite, or boehmite will be preferred when a large external surface is desired and activated alumina will be preferred when it is desirous that the metal oxide/hydroxide have a large internal area.

The use of the term "active material" is intended to define an organic molecule comprising a monomer, oligomer or short chain polymer having a phosphorous-containing group, preferably at the end of the molecule, capable of bonding to the metal oxide/hydroxide support and having one or more sites thereon, preferably at the opposite end of the molecule, which may be used for the coupling, bonding or adsorbing, etc., of atoms, ions or other molecules thereto, e.g., when the active material functions as an adsorbent, the active material will have sites available on the molecule to which the material to be adsorbed will be attracted.

By supercritical fluid chromatography or separation is meant the condition wherein the mobile phase is neither a gas nor liquid but is a fluid subject to pressures and temperatures near its critical point. Under such conditions, the density of the supercritical fluid approaches that of a liquid but its solute diffusion coefficients are higher than that found in liquids, e.g., by as much as two orders of magnitude greater. A supercritical fluid possesses solvating properties similar to a liquid while its solute diffusivities lie between those of gases and liquids.

Typical mobile phases for supercritical fluid chromatography are carbon dioxide, ethane, ethylene, propane, propylene, cyclohexane, isopropanol, benzene, toluene, p-xylene, chlorotrifluoromethane, trichlorofluoromethane, ammonia and water.

Figure 7:
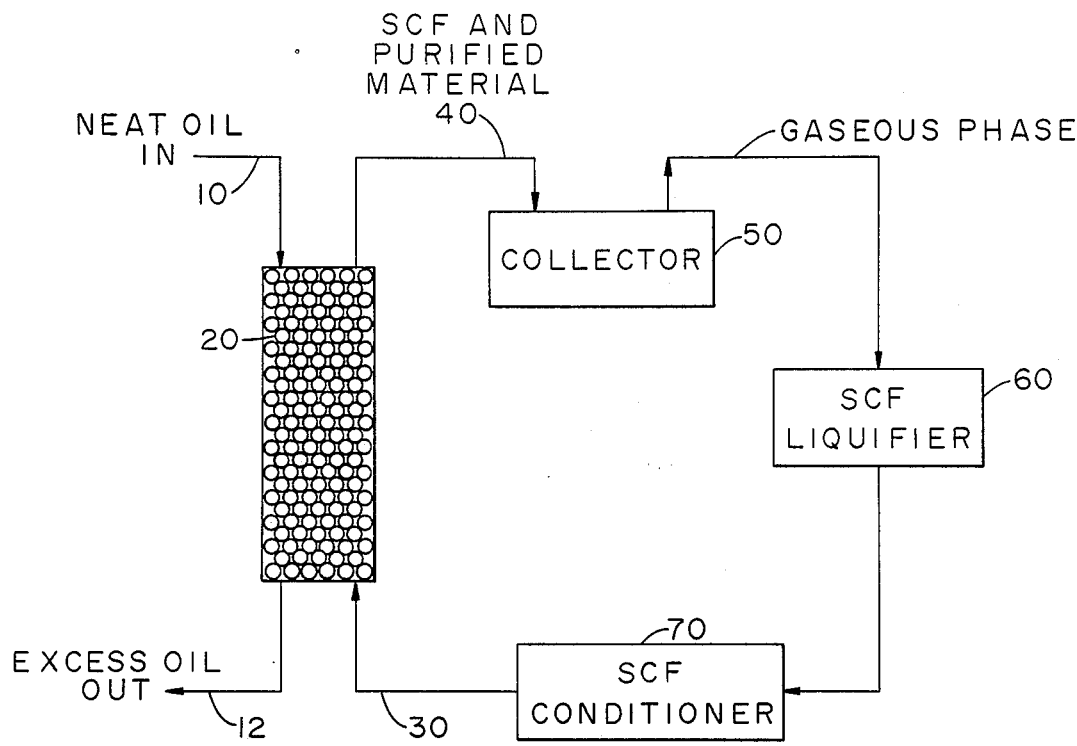
FIG. 7 is a flowsheet illustrating the invention.

In accordance with one aspect of the invention, oil may be purified as shown in FIG. 7. The oil, such as shark liver oil, may be processed neat because solvents can have the tendency to introduce impurities. Oil to be processed is introduced along line 10 into the packed alumina bed or column 20, and excess oil may be removed on line 12. Supercritical fluid such as $CO_2$ at a temperature of 31° C. or greater and at a pressure of 73 atmospheres (atm) or greater is introduced to column 20 along line 30. The shark oil which has been absorbed on the alumina is eluted with supercritical fluid $CO_2$. The desired material such as squalene is then removed with supercritical fluid $CO_2$ along line 40 where it enters a collector 50. In collector 50, the squalene may be separated from the supercritical fluid $CO_2$ by dropping the temperature or the pressure to non-supercritical fluid conditions. The squalene remains in collector 50 and the $CO_2$ in a gaseous condition or phase is then passed to a liquifier or compressor 60. Thereafter, the $CO_2$ may be returned to the packed bed for further extraction or it may be passed through a conditioner or scrubber 70 before being passed to bed 20. It will be understood that for purposes of elution or extraction, the packed column 20 is operated under supercritical fluid conditions. After extraction of the desired material from column 20, the alumina may be regenerated or the remaining material desorbed by back flushing with a liquid such as isopropanol and water or the like. The alumina used in the column can have a surface area in the range of 50 to 500 $m^2/gm$. The alumina may be neutral, activated or doped with a material such as an alkali salt, e.g., sodium- or potassium-containing salts, etc., with activated alumina being preferred for squalene elution. Supercritical fluid conditions for $CO_2$ may be adjusted to provide $CO_2$ at a density in the range of 0.5 to 0.65 gms/ml in column 20. It will be understood that the process may be operated further after removal of the squalene to selectively remove the remaining more polar components, e.g., fatty acids or esters of the shark oil adhered to the alumina. Also, while the process has been illustrated using shark oil with alumina as a packing material, combinations of alumina and carbon or other compounds such as metal oxides/hydroxides such as, for example, magnesium, titanium, zirconium, iron, silicon, chromium, zinc and vanadium and other materials enumerated hereinbelow may be used. Other oils such as olive soil, other fish oils, crude oils, corn oil, for example may be purified or treated in accordance with the invention to recover valuable products, e.g. vitamins.

When derivatized material is used, the metal oxide/hydroxides suitable for use in the present invention usually require hydroxyl groups on the surface thereof for purposes of providing bonding sites for phosphorous-containing phosphonic acids or esters. For example, when the particulate material is alumina, hydroxyl groups on the surface of the alumina react with the phosphorous-containing group of the phosphonic or phosphinic acid or ester molecule, e.g., with the —POOH acid group. When using an organic solvent, particularly where the solvent is immiscible with water, a monolayer of hydroxyl groups are provided on the alumina particles for purposes of reacting to form a chemical bond with the phosphonic acid groups. It will be appreciated that if more than a monolayer of hydroxyl units are present on the alumina surface, such as hydroxyl units present as a result of water, this additional water layer can act to hinder the reaction. Thus, while it is preferred to have a maximum of a monolayer of hydroxyl units, less than a complete surface layer of hydroxyl units can be present on the metal oxide, and such does not hinder reactivity.

Metal oxide/hydroxides which may be used as the support particle for reaction with the phosphonic or phosphinic acids and esters include any metal capable of forming an oxide/hydroxide selected from the class consisting of group IB, group IIA, group IIB, group IIIA, group IIIB, group IVA, group IVB, group VA, group VB, group VIB, group VIIB and group VIII metals, or combinations thereof. In addition, oxides/hydroxides of the lanthanide series, as well as oxides/hydroxides of thorium and uranium in the actinide series, may be used as the support particle. For example, the oxide/hydroxides of aluminum, magnesium, titanium, zirconium, iron, silicon, chromium, zinc, vanadium and combinations of these may be used. Also, a core or center of iron oxide/hydroxide or other paramagnetic or diamagnetic material may be used with a coating of a metal compound to take advantage of the magnetic properties of the iron oxide/hydroxide as an adsorbent. It should be noted that by use of the term "metal", it is intended to include not only the traditional metals, but also materials sometimes referred to as metalloids such as Si, Se, B, As and Te to exclude the remaining elements referred to as nonmetals in the periodic table. In addition, oxides/hydroxides of the lanthanide series as well as oxides/hydroxides of thorium and uranium in the actinide series may be used as the support particle.

To produce the supercritical fluid chromatographic packing material comprising the metal oxide/hydroxide reacted with one or more phosphonic or phosphinic acids or esters, the metal oxide/hydroxide, such as alumina, may be reacted with the acid or ester in an aqueous media at a temperature of from about 25° C. up to about 90° C., preferably about 25° C., for a period of from at least 0.1 to not more than 20 hours, and preferably from at least about 0.5 hours up to about 4 hours, using an initial acid concentration of at least about 0.0001 molar up to about 0.1 molar. In some instances, higher concentrations may be desirable. When the media is nonaqueous, the temperature range can be greatly extended. For example, it may range from 5° C. or lower up to 200° C. or sometimes higher, depending upon the particular liquid media.

When it is desired to produce a monolayer of phosphonic or phosphinic acid or ester on the metal oxide particles, the application should be carefully controlled. That is, a monolayer can be obtained, for example, by controlling the viscosity of the media, the time of exposure in the media, the concentration of phosphorous-bonding hydroxyl units in the media, or the concentration of hydroxyl units on the metal oxide particles.

The supercritical fluid chromatographic packing material used as a column packing material can comprise a metal oxide/hydroxide, preferably aluminum oxide/hydroxide, having a particle size range of from about 0.5–300 microns, preferably about 1–80 microns with a pore diameter size of from 20–100,000 Angstroms, preferably about 40–1000 Angstroms, with a pore volume of about 0.1–2 milliliters/gram, preferably about 0.5–1.5 milliliters/gram, e.g., 0.3 to 0.8 milliliters/gram.

The supercritical fluid packing material can further comprise from 1–75 wt. % (calculated on total weight of the packing material), preferably 4–50 wt. % and typically 5–20 wt. % of one or more phosphonic or phosphinic acids or esters bonded as a monomolecular layer to the reactive sites on the surface of the aluminum oxide/hydroxide support material. The acids or esters bonded to the support material preferably comprise a mixture of from 2 to 97 wt. %, preferably 25–95 wt. %, (based on total weight of phosphonic acids) of one or more phosphonic acids having the formula $RPO(OH)_2$ wherein R is a 5–30 carbon saturated or unsaturated aliphatic hydrocarbon or aromatic hydrocarbon and from 5–75 wt. % of one or more phosphonic acids having the formula $R'PO(OH)_2$ wherein R' is a 1–4 carbon saturated or unsaturated aliphatic hydrocarbon.

Preferably, R' is a single carbon radical, i.e., methyl phosphonic acid which is reacted with the aluminum oxide/hydroxide surface after treatment with the longer chain phosphonic acid to react with any remaining hydroxyl groups on the aluminum oxide/hydroxide surface to provide a good peak symmetry for the materials being passed through the column for analysis.

It will be noted that the R group is always a monomer or oligomer. Preferably, the oligomer has a molecular weight of less than 2000. By the use of monomer herein is meant to include a chemical compound that can undergo polymerization. By oligomer is meant a polymer or polymer intermediate containing relatively few structural units, i.e., a polymer containing 2–4 monomers.

The formulas for the phosphoric acid esters useful in the practice of the invention may be written as $(RO)PO(OH)_2$ (phosphoric acid monoester or monophosphate) while the phosphoric acid diester may be written as $(RO)(R'O)PO(OH)$, R and R' may be organic groups containing 1 to 30 carbon atoms, preferably 5–30, carbon-containing molecules such as an alkyl group. Other examples of groups which may comprise R and/or R' include long and short chain aliphatic hydrocarbons, aromatic hydrocarbons, carboxylic acids, aldehydes, ketones, amines, amides, thioamides, imides, laotams, anilines, pyridines, piperidines, anhydrides, carbohydrates, thiocyanates, esters, lactones, ethers, alkenes, alkynes, alcohols, nitriles, oximes, organosilicones, sulfur containing organic compounds, ureas, thioureas, perfluoro organic molecules, perchloro organic molecules, perbromo organic molecules and combinations of these groups.

While we do not wish to be bound by any particular theory of bonding, it is believed that when a metal oxide/hydroxide particle, for example, alumina, is brought into contact with the phosphonic acid (containing either the long chain or the short chain carbon group previously discussed) a reaction or adsorption of the acid on the alumina takes place in which the aluminum and phosphorus atoms in the respective molecules are apparently bonded together through an oxygen atom as illustrated in the formulas below (in which formula R may represent, for purposes of illustrating the reaction, either the long chain R group or the short chain R' group previously discussed):

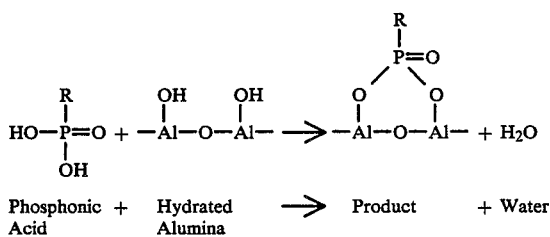

Phosphonic Acid + Hydrated Alumina → Product + Water

It will be appreciated that phosphoric acid monoester or diester will follow the same model with the addition of oxygen between R and P.

Thus it can be seen, using the above proposed model, that if all of the exposed hydroxyl groups on the surface of the alumina can be reacted with the phosphonic acid groups, the surface chemistry of the reacted alumina will be changed. For example, when an alumina treated with a phosphonic acid having a octadecyl R group is used, for example, p-nitroaniline, methyl benzoate, phenetole, and o-xylene under chromatographic conditions can be selectively adsorbed on such a chromatographic packing material in accordance with the present invention.

Figure 8:
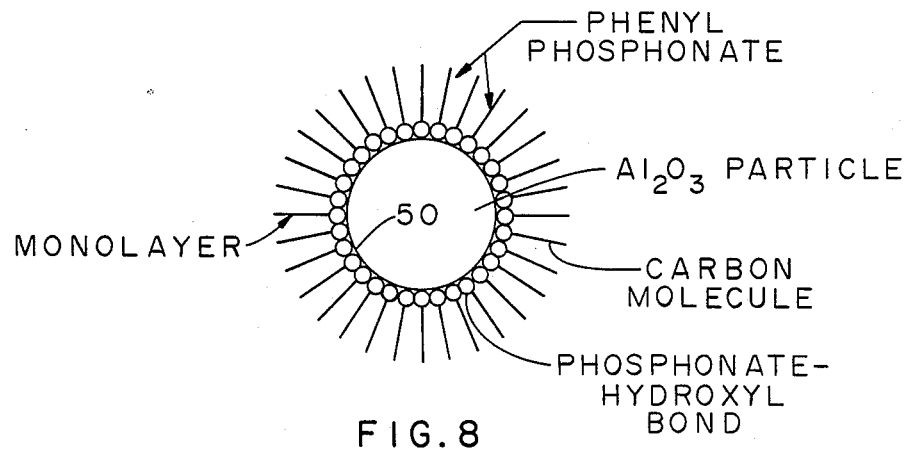
FIG. 8 is an illustration of a metal oxide/hydroxide particle having a monolayer of phosphorous-containing material thereon.

The chemical bonding of the phosphonic acid to the metal oxide/hydroxide particle, e.g., alumina particle, is illustrated in FIG. 8 wherein the center represents the alumina particle having a surface 50. The carbon-containing molecule is chemically bonded at one end to surface 50 by means of a phosphorus-oxygen-metal bond. As presently understood, it is preferred that the other or free end of the carbon-containing molecule extends away from the surface of the particle, as shown in FIG. 8. Further, it is important to control the application or bonding of the phosphonic acid to the metal oxide/hydroxide support so as to obtain a monolayer bonded to the metal oxide/hydroxide particle as illustrated in FIG. 8.

By "monolayer" is meant that 90%, and preferably 98%, of the phosphonic acid molecules are bonded to the metal oxide/hydroxide particle as a monolayer. Thus, the application should be controlled so as to prevent the R or R' groups from bonding to each other to form weakly adsorbed multilayers which would then provide further hydroxyl units, i.e., —POOH units directed away from and not bonded to the metal oxide/hydroxide particles, thereby defeating the purpose of the invention. The thickness of the phosphorous-containing bonded organic monolayer is in the range of 10–5000 Angstroms and preferably 20 to 500 Angstroms.

As noted earlier, while it is desired to avoid organic polymers where the chain has repeating phosphorous-containing groups which can bond to the metal oxide particle surface, oligomers having preferably a single phosphorous-containing group may be used when the group is located at the terminal position. The single phosphorous-bonding group permits the oligomer to have a free end which extends away from the metal oxide particle surface. Additionally, the monomer or oligomer comprising the monolayer may have reactive sites which can permit crosslinking so as to polymerize monomers or oligomers already bonded to the surface of the metal oxide particle.

The available surface area, both outside and inside of the pores, will be somewhat dependent upon the relationship between the pore size of the aluminum oxide/hydroxide support material and the length of the R group on the phosphonic acid. If the pore size is small with respect to the size of the R group on the phosphonic acid molecule, the phosphonic acid may or may not be able to enter into the pores, thereby changing the effective area available for interaction with the organic material being passed through the chromatographic column.

Because of the pores and fissures that can be present on the metal oxide particle, particularly those having high surface area, often all the surface hydroxyl units are not reacted because of the inability of the longer chain phosphorous-containing organic material reaching or diffusing into the pores and fissures. Thus, to insert or block remaining reactive sites, the $R'PO(OH)_2$ phosphonic acid containing the short-chain monomer or oligomer, e.g., 1–4 carbon atoms per chain, is used in a second treatment or reaction. In this way, all of the reactive sites are capped or blocked. That is, for capping off the reactive sites, short-chain monomers can be used. For example, an alumina treated with a high molecular weight phosphonic acid corresponding to the $RPO(OH)_2$ formula, e.g., an n-heltadecylphosphonic acid, may be further treated with a low molecular weight phosphonic acid, e.g., methylphosphonic acid, to treat any remaining unreacted alumina surface areas.

It should be noted in this regard that it is the long chain hydrocarbon R groups, not the short chain R' groups, which principally interact with the respective organic materials being passed through the column to provide the independent peaks identifying the particular organic material passing through the column at various rates of elution. The principal function of the shorter chain R' groups is to react with any remaining hydroxyl groups on the aluminum oxide/hydroxide support material so that the non-polar group or groups of the organic material passing through the column will interact with the non-polar packing materials (rather than the polarized end of the organic molecule passing through the column interacting with exposed hydroxyl groups on the support material). Thus, the shorter chain phosphonic acid must be reacted with the support surface in an amount sufficient to bond to all reactive hydroxyl sites remaining on the support surface after the initial treatment with the one or more longer chain phosphonic acids.

After formation of the packing material, the material may be treated in an organic solvent or a basic or acidic solution, or a combination thereof, e.g., an NaHCO₃-/Na₂CO₃ washing solution having a pH of about 10, to remove any weakly adsorbed molecules on the particles. This ensures that all of the molecules remaining are bonded to the hydroxyl groups on the metal oxide/hydroxide surface and not to one another, thus assuring formation of the desired monomolecular layer stable over a wide range of pH.

The resulting supercritical fluid chromatographic packing material is stable at pH ranges of from 1–14 and has good stability in the range of 2–12 while still maintaining high efficiency of separation. Typically, a supercritical fluid packing based on approximately 10 micron diameter alumina particles with an initial surface area of 150 m²/gram will result in a chromatographic support with an N number of 18,000 to as high as over 25,000 per meter (N being the number of theoretical plates).

The following examples will serve to better illustrate the invention.

Example I

High purity bayerite and gamma alumina were used as supports. The nitrogen BET surface area was 19 and 65 m²/g for bayerite and gamma, respectively. Both the bayerite and gamma aluminas, having an average particle size of about 2 microns, were dried in a 110° drying oven and 10 gram samples were weighed into a number of glass sample vials. To each of four vials containing 10 gram samples of gamma alumina was added, respectively, 100 ml of 0.1, 0.01, 0.001 and 0.0001 molar solutions of phenylphosphonic acid formed by diluting a 0.1 molar phenylphosphonic acid solution with deionized and distilled water. Molar concentrations of 0.01, 0.001 and 0.0001 gave a monolayer but cover less than all of the surface area available on the particles. A molar concentration of 0.1 was sufficient to provide a monolayer on most of the surface area of the particles. Higher than 0.1 molar would have resulted in multilayering, which is undesirable. To a fifth 10 gram sample of gamma alumina was added 100 ml of deionized and distilled water. Five more samples were similarly prepared using 10 gram bayerite samples instead of gamma alumina. The ten samples were shaken and then allowed to age for 24 hours. The contents of the sample containers were then vacuum filtered through Whatman 42 filter paper. The surface modified alumina samples were placed in clean vials and dried in a 110° C. drying oven. The phosphorus content of each of the samples was determined by direct current plasma.

The results are tabulated in Table 1 and plotted in the graph of FIG. 1. It can be seen that there is a significant increase in the amount of phosphorus present on the surface of the bayerite and gamma alumina samples aged in the 0.1 molar solution of phenyl-phosphonic acid compared to less concentrated amounts. Higher phosphorus content of gamma alumina compared to bayerite is because of its higher surface area.

TABLE 1

| Sample Number | Alumina Form | Acid Conc. (M) Molar | Adsorbed Phosphorus Wt. % |
|---|---|---|---|
| 1 | bayerite | 0.0000 | 0.00 |
| 2 | bayerite | 0.0001 | 0.01 |
| 3 | bayerite | 0.001 | 0.01 |
| 4 | bayerite | 0.01 | 0.06 |
| 5 | bayerite | 0.1 | 0.61 |
| 6 | gamma | 0.0000 | 0.00 |
| 7 | gamma | 0.0001 | 0.01 |

TABLE 1-continued

| Sample Number | Alumina Form | Acid Conc. (M) Molar | Adsorbed Phosphorus Wt. % |
|---|---|---|---|
| 8 | gamma | 0.001 | 0.04 |
| 9 | gamma | 0.01 | 0.29 |
| 10 | gamma | 0.1 | 1.85 |

Example II

Figure 6:
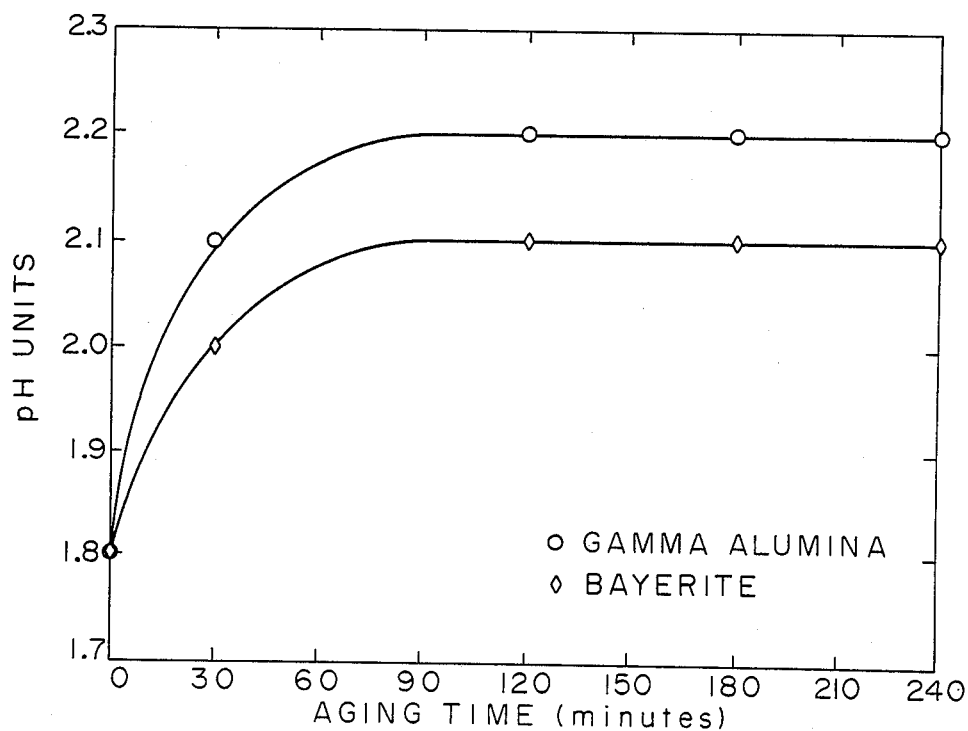
FIG. 6 is a graph of the PH of the solution plotted against time as an indication of phosphorus adsorption on aluminum oxide/hydroxide particles.

Another group of 10 gram samples of gamma and bayerite aluminas were used and to each sample was added 100 ml of 0.1 molar phenylphosphonic acid. Each sample vial was covered and shaken and then allowed to age for a predetermined time period followed by filtration, drying and measurement similar to that previously described in Example I to determine the phosphorus content on the alumina sample with respect to contact time between the respective alumina samples and the phenylphosphonic acid. These results are tabulated in Table 2 and illustrated in the graph of FIG. 2. The filtrate for the alumina samples aged for various time periods was also analyzed for phosphorus content. The concentration of phosphorus in the filtrate of the bayerite and gamma alumina samples aged for various amounts of time is plotted in FIG. 3. The pH change of the respective solution for the gamma and bayerite samples aged for 24 hours was also monitored and the change in pH with respect to time was plotted in FIG. 6 to illustrate yet another way of monitoring the amount of chemically adsorbed phenylphosphonic acid on the aluminas. It is seen that the solution containing the gamma alumina sample shows a rapid rise in pH between 0 and 30 minutes and then a slow increase until 120 minutes where it begins to decrease slightly. The pH of the solution containing the bayerite alumina sample shows linear increase from 0 to approximately 150 minutes and then decreases slightly. It should be noted that aluminas other than bayerite and gamma alumina, e.g., gibbsite, boehmite, eta, chi, rho, delta, kappa and alpha, may be used as supports.

TABLE 2

| Sample Number | Alumina Type | Time in Minutes | Phosphorus Wt. % |
|---|---|---|---|
| 1 | bayerite | 2 | 0.12 |
| 2 | bayerite | 4 | 0.11 |
| 3 | bayerite | 8 | 0.12 |
| 4 | bayerite | 16 | 0.12 |
| 5 | bayerite | 32 | 0.11 |
| 6 | bayerite | 64 | 0.13 |
| 7 | bayerite | 128 | 0.12 |
| 8 | bayerite | 256 | 0.38 |
| 9 | bayerite | 1440 | 1.31 |
| 10 | gamma | 2 | 0.72 |
| 11 | gamma | 4 | 0.62 |
| 12 | gamma | 8 | 0.65 |
| 13 | gamma | 16 | 0.67 |
| 14 | gamma | 32 | 0.62 |
| 15 | gamma | 64 | 0.63 |
| 16 | gamma | 128 | 0.65 |
| 17 | gamma | 256 | 0.80 |
| 18 | gamma | 1440 | 1.56 |

Example III

To further illustrate the practice of the invention, 3 grams each of the filtered and dried gamma alumina samples from Example I, respectively contacted with 01, 0.01 and 0.001 molar phenylphosphonic acid, were washed and filtered 3 times with 30 ml of distilled, deionized water. Filtered and dried 3 gram gamma alumina samples from Example II which had, respectively, been contacted with 0.1 molar phenylphosphonic acid for 8, 64 and 1440 minutes were similarly washed. All the washed samples were then placed into clean vials and dried in a 110° C. drying oven. The gamma alumina samples contacted with the 0.1 molar concentration phenylphosphonic acid were not wettable. They were also not affected by the washing.

Figure 2:
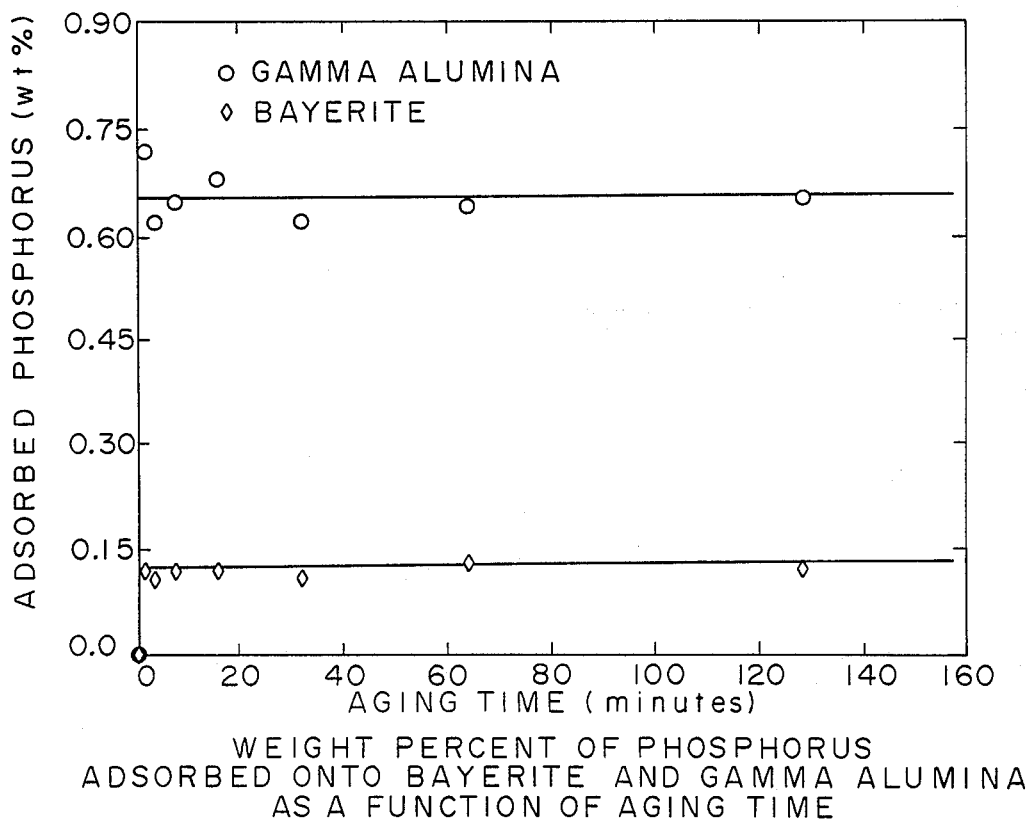
FIG. 2 is a graph showing the weight percent of phosphorus adsorbed to forms of aluminum oxide/hydroxide as a function of aging time.
Figure 3:
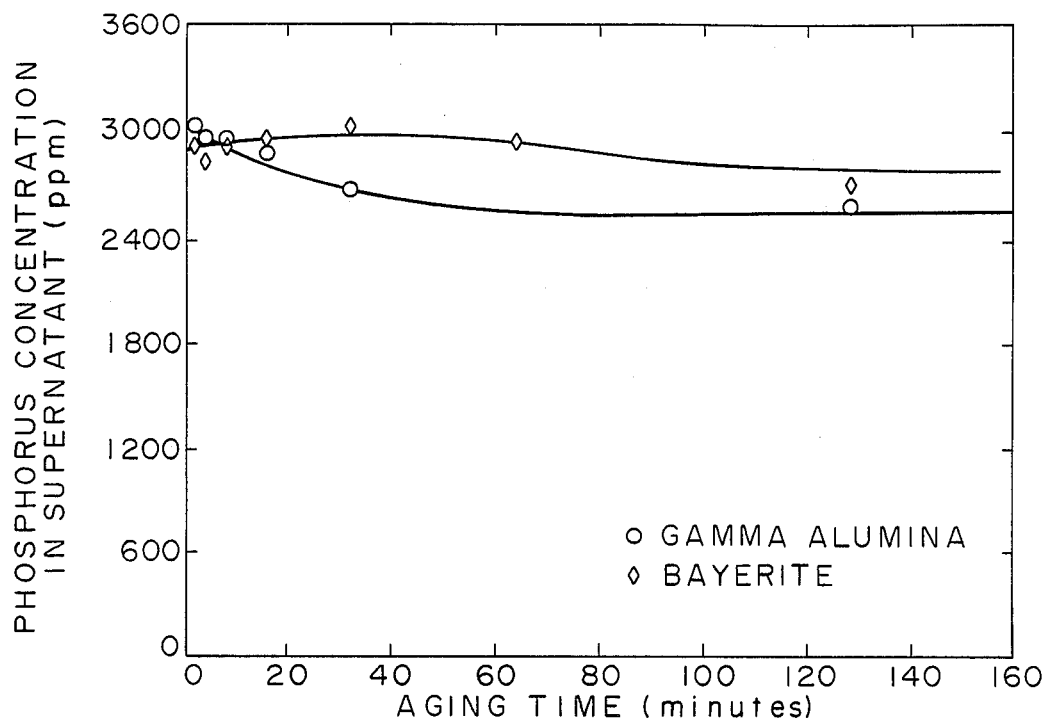
FIG. 3 is a graph showing the concentration of phosphorus remaining in solution after filtration as a function of aging time.
Figure 4:
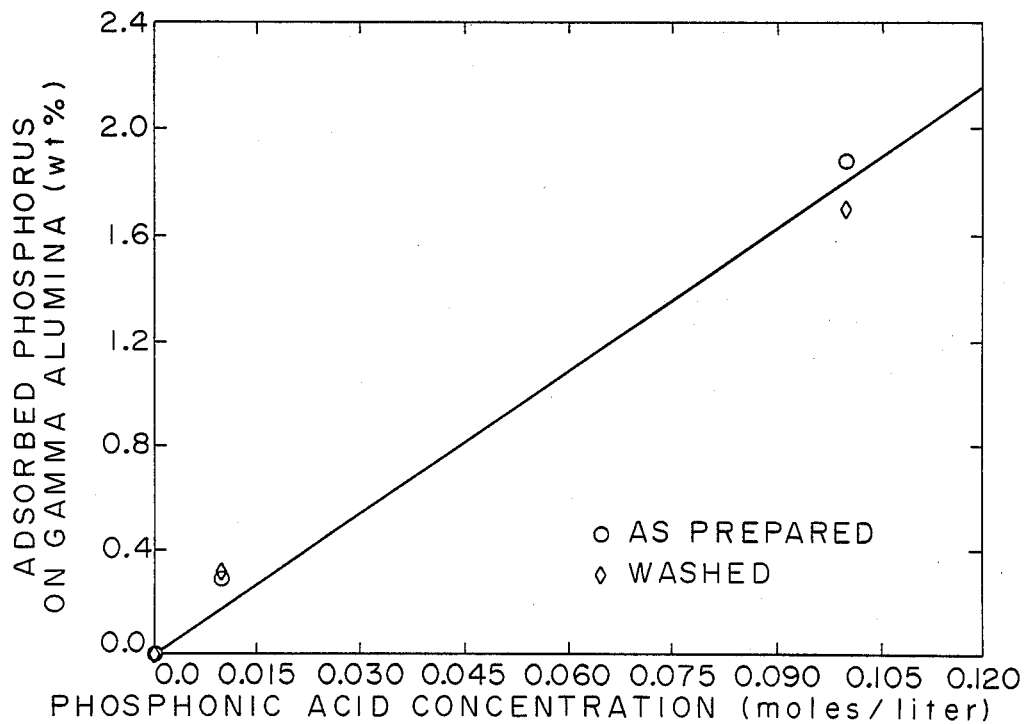
FIG. 4 is a graph showing the weight percent of phosphorus adsorbed to gamma alumina before and after washing as a function of acid concentration.
Figure 5:
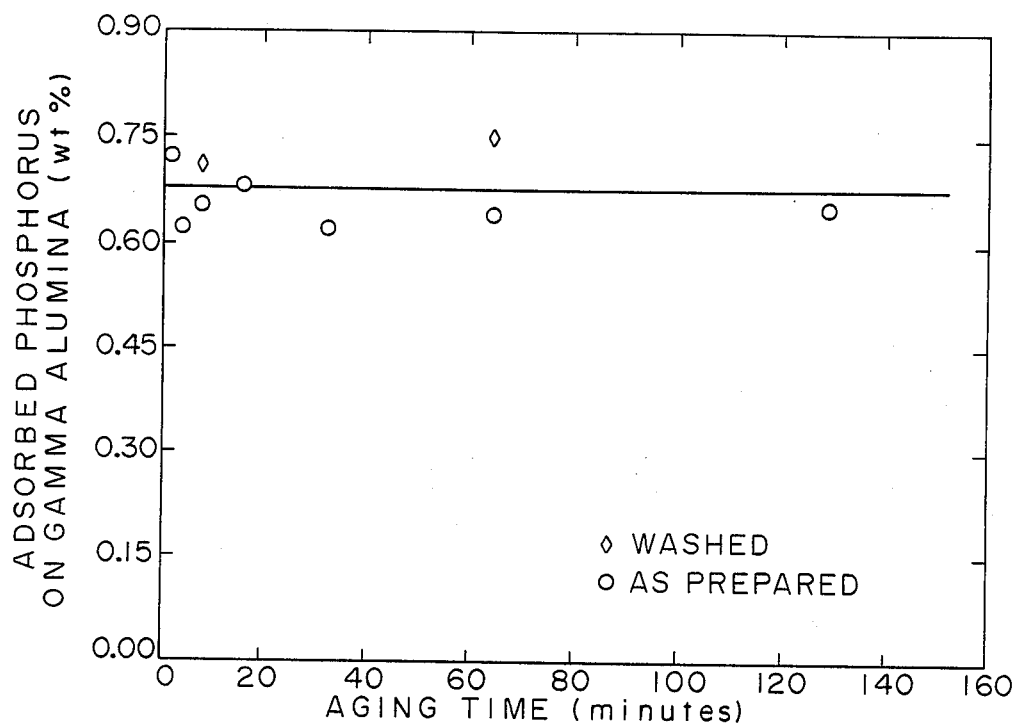
FIG. 5 is a graph showing the weight percent of phosphorus adsorbed to gamma alumina before and after washing as a function of aging time.

The results are respectively illustrated in FIGS. 4 and 5 in which the results from the washed samples are plotted in dotted lines superimposed on the respective solid line gamma curves for unwashed samples corresponding to the gamma curves respectively shown in FIGS. 1 and 2. It will be noted that the amount of phosphorus remaining on the treated alumina after washing is fairly comparable to the unwashed samples.

Example IV

To illustrate the multiple treatment of alumina with more than one type of phosphonic or phosphinic acid, a solution of 0.1 molar n-heptadecylphosphonic acid was prepared by dissolving 3.8454 grams in 120 ml. of isopropanol at 45° C. Thirty grams of activated 7–12 micron alumina was weighed into this solution which was then shaken to mix and placed in an ultrasonic bath for 15 minutes. The mixture was vacuum filtered through Whatman #3 filter paper. The alumina was washed with 3 volumes of isopropanol and placed in an oven at 110° C. to dry. The unreacted sites on the surface of the alumina were then capped with methylphosphonic acid. A solution of 0.1 molar methyl phosphonic acid was prepared by dissolving 1.1524 grams of methylphosphonic acid in 120 ml of isopropanol at 45° C. The dried n-heptadecylphosphonic acid loaded alumina was added to this, shaken to mix, and placed in an ultrasonic bath for 15 minutes. The alumina was then again filtered, washed and dried at 110° C.

Another alumina sample was then contacted with a 0.3 molar solution of n-heptadecylphosphonic acid dissolved in isopropanol under the same conditions and then capped as above with a 0.1 molar solution of methylphosphonic acid.

Both samples were analyzed on an IBM Instruments IR-98 Foourier Transform Infrared Spectrometer with 128 scans per spectrum at 4 cm-1 resolution. The spectra were plotted using a KBr spectrum as reference. The bands chosen for the n-heptadecylphosphonic acid calibration curves were the 2928 cm-1 asymmetric stretching band and the 1470 cm-1 bending band. The band at 1470 cm-1 is selected as the analytical wavelength because the value for its standard deviation is ten times less than the value for the band at 2928 cm-1. At this wavelength, the respective weight percent of n-heptadecylphosphonic acid loaded by treating the alumina with the 0.1 molar and 0.3 molar solutions was 6.88 and 24.85 wt. %, respectively.

Example V

To separate squalene from shark liver oil, a supercritical fluid column was set up substantially as shown in FIG. 7. The column was packed with 10 gms of alumina, and 1 gm of shark liver oil was adsorbed onto the alumina. Supercritical $CO_2$ was passed through the column and squalene was eluted from shark oil. The squalene was separated from the $CO_2$ in the squalene collector by dropping the $CO_2$ to ambient temperature (about 25° C). The $CO_2$ was then heated to slightly above 31° C. while maintaining the pressure above 73 atms and then recirculated through the packed column. The recirculation processing was carried out for 10 minutes, and the density of the supercritical $CO_2$ was maintained at about 0.6 gms/ml. The squalene eluted and collected had a purity of greater than 99%. Further, the shark oil remaining after elution was removed by backflushing with isopropanol/water mix (80:20). Thus, it is seen that squalene can be removed from shark liver oil by the use of supercritical $CO_2$. Fatty acids and esters may also be removed after the squalene by varying the density of the $CO_2$ passing through the column.

The chromatographic measurements showing sharp peaks are shown in FIGS. 9a through 9d. FIG. 9a is a measurement of the neat shark oil after supercritical fluid separation. FIG. 9b shows peaks for neat saponified shark liver oil subjected to supercritical fluid separation in the same manner. FIG. 9c shows the peaks obtained when squalene and hexane was added to shark liver oil and treated as in this Example. FIG. 9d shows the results when shark liver oil was diluted with hexane prior to subjecting to supercritical fluid separation.

Thus, the invention provides an improved reverse phase chromatographic packing material which exhibits good stability over a wide pH range with good separation efficiency.

Having thus described the invention, what is claimed is:

1. A method of separating organic materials or organometallic materials under supercritical fluid conditions, the method comprising the steps of:
    (a) providing a bed of packing material selected from a metal oxide/hydroxide support material having esters or acids of phosphorous-containing organic molecules bonded to reactive sites on said support material;
    (b) introducing organic materials or organometallic materials to the bed;
    (c) adding an eluting fluid to said bed under supercritical fluid conditions;
    (d) removing said fluid and one of said organic materials or organometallic materials from the bed; and
    (e) separating said material removed in step (d) from the fluid by returning the fluid to nonsupercritical conditions.

2. The method in accordance with claim 1 wherein the fluid is $CO_2$.

3. The method in accordance with claim 2 wherein the $CO_2$ is maintained at a temperature of greater than 31° C. and a pressure of greater than 73 atms for supercritical fluid conditions.

4. The method in accordance with claim 2 wherein separation is performed by returning the fluid to a non-critical condition.

5. The method in accordance with claim 1 wherein the organic material is shark liver oil.

6. The method in accordance with claim 5 wherein the organic material eluted from the shark liver oil is squalene.

7. The method in accordance with claim 1 wherein the support material has a surface area in the range of 50 to 500 m2/g.

8. The method in accordance with claim 1 wherein the organic materials have some components less polar than others.

9. The method in accordance with claim 8 wherein the less polar compound is removed first.

10. The method in accordance with claim 1 wherein the acid has the formula $RPO(OH)_2$ where R comprises a carbon containing group.

11. The method in accordance with claim 10 wherein the R or R' group may comprise an organic radical selected from the class consisting of long and short chain aliphatic hydrocarbons, aromatic hydrocarbons, carboxylic acids, aldehydes, ketones, amines, amides, thioamides, imides, lactams, anilines, pyridines, piperidines, anhydrides, carbohydrates, esters, lactones, ethers, alkenes, alkynes, alcohols, nitriles, oximes, organosilicones, sulfur containing organic compounds, ureas, thioureas, perfluoro, perchloro, perbromo organic molecules and combinations of these groups.

12. The method in accordance with claim 10 wherein either said R group or said R' group may have a functional group attached to a portion of said molecule spaced from said phosphorous-containing group on said molecule selected from the class consisting of a carboxyl group, a glucose group, a monoclonal antibody, a cyano group, a cyanate group, isocyanate group and thiocyanate group, a phenyl group, a diphenyl group, a tertiary butyl group, a sulfonic group, a benzyl sulfonic group, a protein group pharmaceutical compounds, yeasts, microbes, whole cells, an enzyme group, a dye group, a chelated metal group, a tag molecule, a halogen group, nitrate group, phosphate group, phosphinate group, phosphinite group, phosphonate group, quaternary ammonium salt group and combinations of these groups.

13. The method in accordance with claim 1 wherein the ester has 1-2 phosphorous-containing groups thereon selected from the class consisting of:
    (a) phosphoric acid monoester having a formula $(RO)PO(OH)_2$; and
    (b) phosphoric acid diester having a formula $(RO)(R'O)PO(OH)$;
where R comprises a carbon-containing group and R' comprises a carbon-containing group.

14. The method in accordance with claim 13 wherein the R or R' group may comprise an organic radical selected from the class consisting of long and short chain aliphatic hydrocarbons, aromatic hydrocarbons, carboxylic acids, aldehydes, ketones, amines, amides, thioamides, imides, lactams, anilines, pyridines, piperidines, anhydrides, carbohydrates, esters, lactones, ethers, alkenes, alkynes, alcohols, nitriles, oximes, organosilicones, sulfur containing organic compounds, ureas, thioureas, perfluoro, perchloro, perbromo organic molecules and combinations of these groups.

15. The method in accordance with claim 13 wherein either said R group or said R' group may have a functional group attached to a portion of said molecule spaced from said phosphorous-containing group on said molecule selected from the class consisting of a carboxyl group, a glucose group, a monoclonal antibody, a cyano group, a cyanate group, isocyanate group and thiocyanate group, a phenyl group, a diphenyl group, a tertiary butyl group, a sulfonic group, a benzyl sulfonic group, a protein group pharmaceutical compounds, yeasts, microbes, whole cells, an enzyme group, a dye group, a chelated metal group, a tag molecule, a halogen group, nitrate group, phosphate group, phosphinate group, phosphinite group, phosphonate group, quaternary ammonium salt group and combinations of these groups.

16. The method in accordance with claim 1 wherein the support material is a metal oxide/hydroxide particle which comprises an oxide/hydroxide of an element capable of forming an oxide/hydroxide selected from the class consisting of group IB, group IIA, group IIB, group IIIA, IVA, VA, group IIIB, group IVB, group IVB, group VB, group VIB, group VIIB, and group VIII metals; lanthanide series; silicon, boron, selenium, arsenic and tellurium.

17. The method in accordance with claim 1 wherein the metal oxide/hydroxide particles comprise an oxide/hydroxide of a metal selected from the class consisting of aluminum, magnesium, titanium, zirconium, iron, silicon, chromium, zinc, vanadium, and combinations of these metals.

18. The method in accordance with claim 1 wherein the metal oxide/hydroxide particles are selected from the class consisting of alumina, iron oxide, silica, zeolitic materials, zirconia, zinc oxide, magnesia, apatites, and hydrotalcites.

19. The method in accordance with claim 11 wherein the metal oxide/hydroxide particles comprise alumina.

20. The method in accordance with claim 1 wherein the support material has a monomolecular layer of organic material 21. A method of separating squalene from shark liver oil under supercritical fluid conditions, the method comprising the steps of:
    (a) providing a bed containing alumina particles having bonded thereto an organic molecule comprised of a phosphoric group selected from acids and esters chemically bonded to reactive sites on the support material;
    (b) introducing shark liver oil to the bed;
    (c) adding $CO_2$ to said bed under supercritical fluid conditions;
    (d) removing $CO_2$ and squalene from the bed; and
    (e) separating the squalene from the $CO_2$ by returning the $CO_2$ to nonsupercritical conditions.

* * * * *